United States Patent
Maarek

(10) Patent No.: US 9,629,559 B2
(45) Date of Patent: Apr. 25, 2017

(54) MEASURING HOMEOSTATIC RISK

(71) Applicant: Medical Screening Corporation, Miami, FL (US)

(72) Inventor: Albert Maarek, Miami, FL (US)

(73) Assignee: MEDICAL SCREENING CORPORATION, Miami, FL (US)

( * ) Notice: Subject to any disclaimer, the term of this patent is extended or adjusted under 35 U.S.C. 154(b) by 0 days.

(21) Appl. No.: 15/082,823

(22) Filed: Mar. 28, 2016

(65) Prior Publication Data
US 2016/0206213 A1 Jul. 21, 2016

Related U.S. Application Data

(63) Continuation-in-part of application No. 14/681,297, filed on Apr. 8, 2015, which is a continuation-in-part
(Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0295* (2013.01); *A61B 5/02405* (2013.01);
(Continued)

(58) Field of Classification Search
CPC ........................ A61B 5/0205; A61B 5/0295
See application file for complete search history.

(56) References Cited

U.S. PATENT DOCUMENTS

2006/0074333 A1* 4/2006 Huiku ................. A61B 5/0205 600/529
2009/0292180 A1* 11/2009 Mirow ................. G06F 19/363 600/301
(Continued)

OTHER PUBLICATIONS

"ES-TECK System General Information's" slideshow uploaded by inov8solutions, [HTTP: http://www.slideshare.net/inov8solutions/68-132].*
(Continued)

*Primary Examiner* — William Thomson
*Assistant Examiner* — Amanda Steinberg
(74) *Attorney, Agent, or Firm* — Mark Terry

(57) ABSTRACT

A method and system for determining homeostatic risk in a patient, in order to screen metabolic diseases and/or their complications and/or their treatment management, is provided. The method includes receiving, from one or more sensors coupled with the patient, galvanic skin response, bioimpedance, a photoplethysmogram (PTG), and blood pressure from the patient, calculating a first score based on the PTG, calculating a second score based on the galvanic skin response, calculating a third score based on the bioimpedance, calculating a fourth score based on the blood pressure, calculating a homeostatic risk score based on the first, second, third and fourth scores that were calculated, wherein the homeostatic risk score corresponds to the homeostatic risk of the patient, and displaying the homeostatic risk score.

10 Claims, 12 Drawing Sheets

Related U.S. Application Data of application No. 14/259,282, filed on Apr. 23, 2014, now abandoned, which is a continuation of application No. 13/514,353, filed as application No. PCT/IB2010/003114 on Dec. 6, 2010, now abandoned, application No. 15/082,823, which is a continuation-in-part of application No. PCT/IB2013/002595, filed on Nov. 21, 2013, application No. 15/082,823, which is a continuation-in-part of application No. PCT/IB2014/001047, filed on Dec. 6, 2012.

(60) Provisional application No. 61/267,510, filed on Dec. 8, 2009, provisional application No. 61/267,542, filed on Dec. 8, 2009, provisional application No. 61/728,848, filed on Nov. 21, 2012.

(51) Int. Cl.
  *A61B 5/0295* (2006.01)
  *A61B 5/024* (2006.01)
  *A61B 5/053* (2006.01)
  *A61B 5/145* (2006.01)

(52) U.S. Cl.
  CPC .......... *A61B 5/0533* (2013.01); *A61B 5/4035* (2013.01); *A61B 5/4848* (2013.01); *A61B 5/7257* (2013.01); *A61B 5/7275* (2013.01); *A61B 5/742* (2013.01); *A61B 5/14542* (2013.01)

(56) References Cited

U.S. PATENT DOCUMENTS

| | | | | |
|---|---|---|---|---|
| 2010/0057490 | A1* | 3/2010 | Kocis | G06F 19/345 705/2 |
| 2010/0081941 | A1* | 4/2010 | Naghavi | A61B 5/015 600/481 |
| 2012/0108928 | A1* | 5/2012 | Tverskoy | A61B 5/0059 600/324 |
| 2013/0053721 | A1* | 2/2013 | Brunswick | A61B 5/0531 600/547 |

OTHER PUBLICATIONS

Lewis, "Comparing the accuracy of ES-BC, EIS-GS, and ES Oxi on body composition, autonomic nervous system activity, and cardiac output to standardized assessments", MDER, p. 169, 2011.*

Khalfallah, H. Ayoub, J. Calvet, X. Neveu, P. Brunswick, S. Griveau, V. Lair, M. Cassir and F. Bedioui, "Noninvasive Galvanic Skin Sensor for Early Diagnosis of Sudomotor Dysfunction: Application to Diabetes", IEEE Sensors J., vol. 12, No. 3, pp. 456-463, 2010.*

* cited by examiner

MEASURING HOMEOSTATIC RISK

CROSS-REFERENCE TO RELATED APPLICATIONS

This patent application is a continuation in part of patent application Ser. No. 14/681,297, filed Apr. 8, 2015, and entitled "Medical Device," which is a continuation in part of, and claims priority to, patent application Ser. No. 14/259,282, filed Apr. 23, 2014, which is a continuation of, and claims priority to, patent application Ser. No. 13/514,353, filed Oct. 10, 2012, which is a national stage filing of, and claims priority to, international application number PCT/IB2010/003114, filed Dec. 6, 2010, which claims priority to patent application No. 61/267,510, filed Dec. 8, 2009, wherein international application number PCT/IB2010/003114 also claims priority to patent application No. 61/267,542, filed Dec. 8, 2009. This patent application is also a continuation in part of, and claims priority to, international application number PCT/IB2013/002595, filed Nov. 21, 2013, and entitled "Method and Apparatus for Detection of Insulin Resistance, Diabetes and Cardiovascular Disease," which claims priority to provisional patent application No. 61/728,848, filed on Nov. 21, 2012. This patent application is also a continuation in part of, and claims priority to, international application number PCT/IB2014/001047, filed Dec. 6, 2014, which claims priority to provisional patent application No. 61/835,064, filed on Jun. 14, 2013.

The subject matter of patent application numbers Ser. Nos. 14/681,297, 14/259,282, 13/514,353, PCT/IB2010/003114, 61/267,510, 61/267,542, PCT/IB2013/002595, 61/728,848 PCT/IB2014/001047, and 61/835,064 are hereby incorporated by reference in their entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to the field of healthcare and, more specifically, relates to the field of diagnostic tests used for providing a health assessment.

BACKGROUND

Chronic metabolic diseases such as diabetes, and its frequent complications, such as cardiovascular disease and autonomic neuropathy, have become epidemics in the United States. Tens of millions of Americans live with diabetes, cardiovascular disease and autonomic neuropathy. A majority of these individuals have been living with these afflictions for multiple numbers of years. The loss of productivity and daily activity due to these diseases is substantial. Additionally, it has been estimated that millions of individuals see a physician for treatment of these maladies every year. Additional millions will develop diabetes, cardiovascular disease and autonomic neuropathy in the near future. Thus, our healthcare system is significantly affected by the amount of resources that are allocated to treat diabetes, cardiovascular disease and autonomic neuropathy each year.

The aforementioned diseases correlate to the autonomic nervous system and the endothelial functions of a patient. The autonomic nervous system (ANS) is an extensive neural network whose main role is to regulate a patient's internal environment and bodily functions by controlling homeostasis, which includes hemodynamics, blood pressure, heart rate, blood glucose level, sweating and visceral functions. The ANS acts through a balance of stimulation or inhibition of its own two components—the sympathetic and parasympathetic nervous systems. Sympathetic and parasympathetic branches act via neurotransmitters and receptors activation. The endothelial functions of a patient are related to the ability of the blood vessels to dilate when necessary. Endothelial dysfunction can be defined as reduced bioavailability of nitric oxide (NO), which plays many roles in maintaining vascular health, most importantly its role in vasomotor functions. Hence, endothelial dysfunction is defined as an impairment of endothelium dependent vasodilation. Homeostasis is supported by the ANS and endothelial functions of the body.

As stated by Lippincott: "Disease or death is often the result of dysfunction of internal environment and regulatory mechanisms. Understanding the body's processes, responses and functions is clearly fundamental to the intelligent practice of medicine." The current clinical contexts, lab tests, functional tests (such as EKG or Doppler) and imagery available provide doctors a certain amount of data to establish diagnoses and treatment plans on predictions based upon recognized scientific background and practitioner decision. None of these analyses, however, take into account the overall potential of the regulatory abilities of the individual patient. Without knowing a patient's potential adaptation to a dysfunction or disease, it is difficult to formulate a well-informed treatment plan.

In general, treatment for diabetes, cardiovascular disease and autonomic neuropathy can be more effective if these diseases are diagnosed accurately and early. Currently, however, the approaches available for diagnosing these maladies can be costly, time-consuming, inaccurate and imprecise. Further, there is no diagnostic process for these diseases that takes multitudes of factors into account, such as a patient's regulatory abilities. Another problem associated with the detection of said diseases is the lack of a generally-accepted paradigm for diagnosing diabetes, cardiovascular disease and autonomic neuropathy precisely. In the medical field, this leads to a great disparity in how diabetes, cardiovascular disease and autonomic neuropathy are diagnosed, charged and conducted.

Therefore, what is needed is a system and method for improving upon the problems with the prior art, and more particularly for a more efficient and precise way of measuring a patient's regulatory abilities in order to screen metabolic chronic diseases and/or their complications and/or their treatment management.

SUMMARY

A method and system for determining homeostatic risk in a patient, in order to screen metabolic diseases and/or their complications and/or their treatment management, is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, the method and system include the following steps: receiving, from one or more sensors coupled with the patient, galvanic skin response, bioimpedance, a photoplethysmogram (PTG), and blood pressure from the patient; executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG; calculating PTG Total Power (PTGTP) as the sum of PTGHF, PTGLF, and PTGVLF; calculating PTG index (PTGi) of the spectral analysis as a sum of amplitudes of the PTGHF, PTGLF, and PTGVLF; calculating PTG VLF index (PTGVLFi) of the spectral analysis as PTGVLF divided by a value derived from the galvanic skin response; calculating PTG ratio (PTGr) of the spectral analysis as PTGVLF divided by PTGi; calculating a heart rate variability based on the PTG and calculating a stress index based on the heart rate variability; calculating −da, reflection index (RI), left ventricular ejection time (LVET) and pre-ejection period (PEP) based on the PTG; calculating a first score based on PTGTP, stress index, PTGLF, PTGHF, RI, −da, PEP, LVET, PTGi, PTGVLFi, and PTGr; calculating electro skin response nitric oxide (ES-RNO), electro skin response latency (ESRL) and Peak C based on the galvanic skin response; calculating a second score based on the ESRNO, ESRL and the Peak C; calculating body mass index (BMI) fat mass based on the bioimpedance; calculating a third score based on the BMI and fat mass; calculating systolic pressure, diastolic pressure and ankle-brachial index (ABI) based on the blood pressure; calculating a fourth score based on the systolic pressure, diastolic pressure and ABI; calculating a homeostatic risk score based on the first, second, third and fourth scores that were calculated, wherein said homeostatic risk score corresponds to the homeostatic risk of the patient; and displaying the homeostatic risk score.

BRIEF DESCRIPTION OF THE DRAWINGS

The accompanying drawings, which are incorporated in and constitute a part of this disclosure, illustrate various example embodiments. In the drawings.

DETAILED DESCRIPTION

Figure 1:
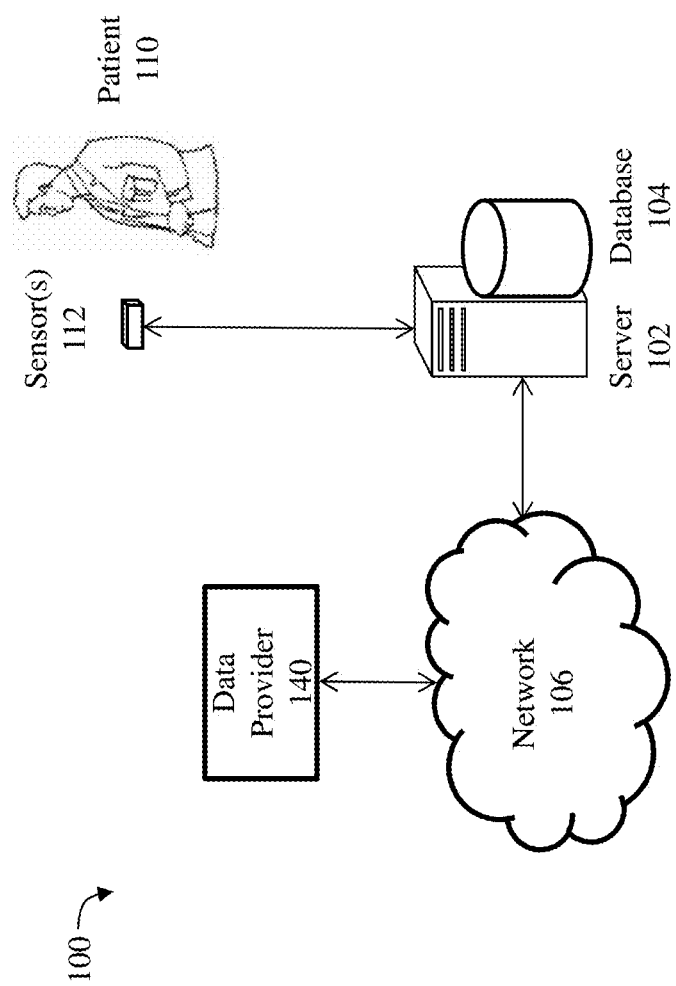
FIG. 1 is a block diagram of an operating environment that supports a method and system for calculating a homeostatic risk score in a patient, according to an example embodiment.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves upon the problems with the prior art by providing a system and method for allowing a physician or other healthcare professional to accurately calculate a homeostatic risk score for a patient in a timely and economically feasible manner, in order to screen metabolic diseases and/or their complications and/or their treatment management. The homeostatic risk score corresponds to the patient's risk associated with said metabolic diseases, and their complications, as well as the treatment of said diseases. Further, the claimed subject matter provides a precise and automated way to calculate a homeostatic risk score in a patient, wherein the process takes multitudes of factors into account, such as bioimpedance and galvanic skin response data collected from the patient. Also, the claimed subject matter provides a standardized paradigm for calculating a homeostatic risk score in a patient.

The claimed subject matter improves upon the problems with the prior art by establishing an overall potential of auto regulation of the patient, by assigning a score to be known as the homeostatic risk score. The homeostatic risk score provides a quick and accurate overview of a patient's homeostasis processes and responses, using key indicators, to understand the patient's potential adaptation to lifestyle, disorders, diseases and any current treatments. The claimed subject matter further provides cost effective therapeutic adjustment and follow up. Said claimed homeostasis evaluation allows a healthcare professional to test how a planned treatment would affect a patient, resulting in saved time, and as the possibilities of treating diseases improve, one may select the right treatment for each individual patient.

FIG. 1 is a block diagram of an operating environment 100 that supports a method and system for calculating a homeostatic risk score in a patient, according to an example embodiment. The environment 100 may comprise at least two computing devices 140, 112 and a server 102, which may communicate via a communications network 106. The computing devices 140, 112, 102 may be connected either wirelessly or in a wired or fiber optic form to the communications network 106. The at least one sensor 112 may be communicatively coupled, either wirelessly or in a wired or fiber optic form to the server 102. Communications network 106 may be a packet switched network, such as the Internet, or any local area network, wide area network, enterprise private network, cellular network, phone network, mobile communications network, or any combination of the above.

Sensor 112 and computing devices 140, 102 may each comprise a computing device 600, described below in greater detail with respect to FIG. 6. In one embodiment, at least one sensor 112 may be a pulse oximeter device, a galvanic skin response device, a blood pressure monitor device, and a bioimpedance measuring device, all of which record data from a patient 110. In another embodiment, at least one sensor 112 may include functions that record other vital information of patient 110, such as temperature, heart rate, wattage output, lung capacity, skin suppleness, breathing rate, etc. Further, sensor 112 and computing devices 140, 102 may each comprise mobile computing devices such as cellular telephones, smart phones, tablet computers, wearable devices, or other computing devices such as a desktop computer, laptop, game console, etc. In one embodiment, the at least one sensor 112 may be integrated with computing device 102.

Server 102 includes a software engine that delivers applications, data, program code and other information to networked devices 112, 140. The software engine of server 102 may perform other processes such as transferring multimedia data, such as audio and video, in a stream of packets that are interpreted and rendered by a software application as the packets arrive. It should be noted that although FIG. 1 shows only a certain number of computing devices, the disclosed system supports any number of computing devices that may be connected via network 106.

Server 102, and computing devices 112, 140 may each include program logic comprising computer source code, scripting language code or interpreted language code that perform various functions. In one embodiment, the aforementioned program logic may comprise program module 607 in FIG. 6.

FIG. 1 further shows that server 102 includes a database or repository 104, which may be a relational database comprising a Structured Query Language (SQL) database stored in a SQL server. Computing devices 112, 140 may also each include databases. The database 104 may serve data used by server 102, computing devices 112, 140 during the course of operation of the disclosed systems and methods.

Environment 100 may be used when the disclosed computing devices transfer data to and from database 104 coupled to server 102. Various types of data may be stored in the database 104 of server 102. For example, the database 104 may store one or more patient records for each patient, i.e., a patient record. A patient record may include personal data for the patient 110, which may include contact information for a patient 110, a medical history of the patient, demographic data of the patient, clinical data of the patient, and psychological data of the patient and occupational data of the patient. A patient record may also include assessment data for the patient, wherein the assessment data includes medical assessment data of the patient, functional assessment data of the patient, psychological assessment data of the patient and economic assessment data of the patient, or the like. A patient record may also include risk data based on the personal data for the patient 110, wherein the risk data defines the patient's risk of further developing a current affliction or having a recurrence of the current affliction, and result data based on the assessment data for the patient, wherein the result data defines a result of the exercise regimen in treating the current affliction.

Note that although server 102 is shown as a single and independent entity, in one embodiment, the functions of server 102 may be integrated with another entity, such as the computing device 112, 140. Further, server 102 and its functionality, according to a preferred embodiment, can be realized in a centralized fashion in one computer system or in a distributed fashion wherein different elements are spread across several interconnected computer systems.

Figure 2:
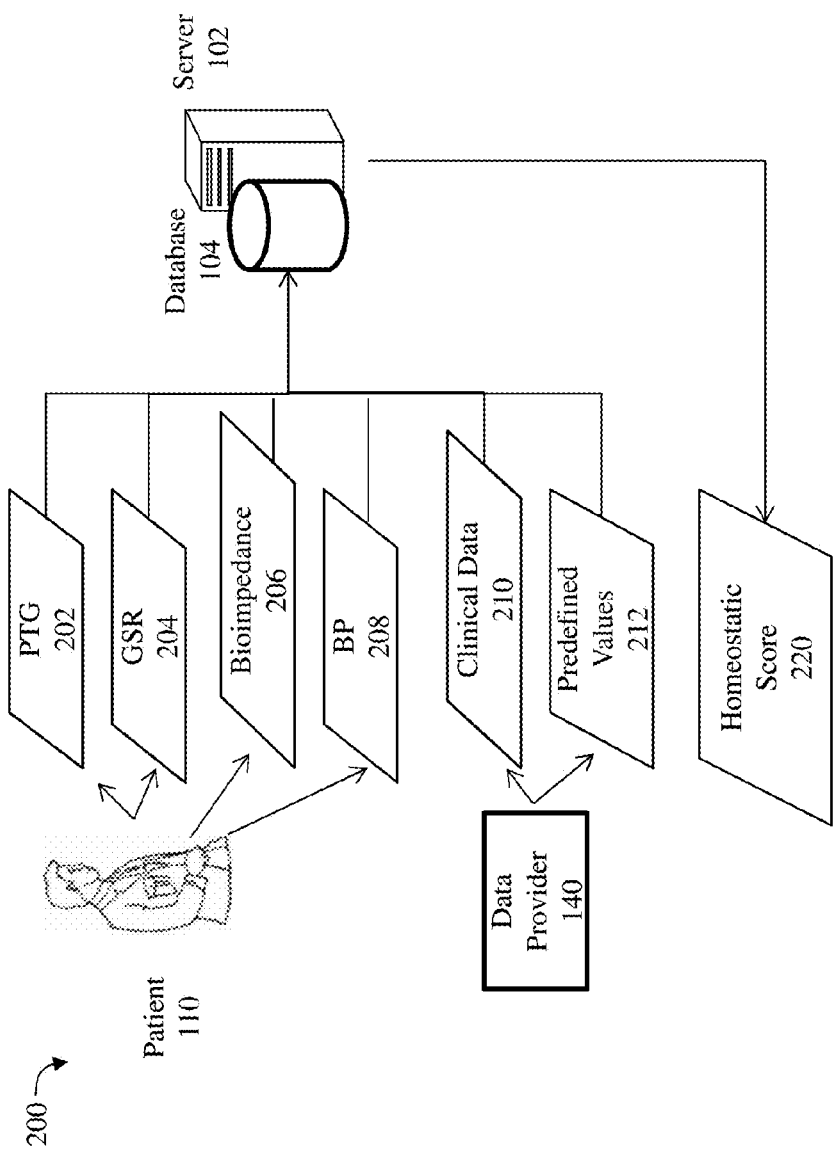
FIG. 2 is a diagram showing the data flow of the method and system for calculating a homeostatic risk score in a patient, according to an example embodiment.
Figure 3:
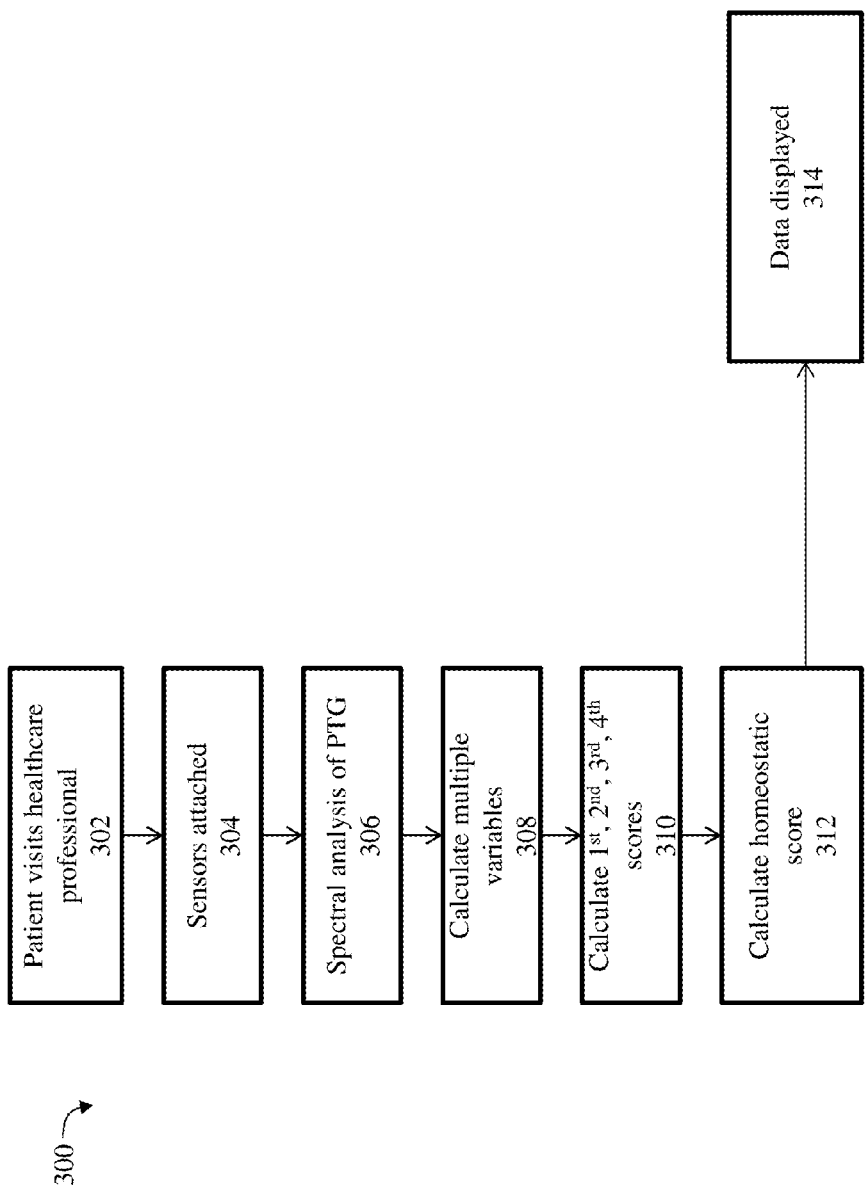
FIG. 3 is a flow chart of a method for calculating a homeostatic risk score in a patient, according to an example embodiment.

FIG. 3 is a flow chart of a method 300 for calculating a homeostatic risk score in a patient, in order to screen metabolic diseases and/or their complications and/or their treatment management, according to an example embodiment. Method 300 describes the steps that occur when a patient 110 undergoes evaluation or diagnosis by a healthcare professional, wherein the evaluation or diagnosis process is facilitated by the use of environment 100. The method 300 is described with reference to FIG. 2, which is a diagram 200 showing the data flow of the process for facilitating diagnosis or evaluation of patients, according to an example embodiment.

In an optional preliminary step, the method 300 begins with the database 104 receiving (such as via network 106) and storing clinical data 210 and predefined values 212 from, for example, a data provider 140, which may be a third party provider of data. Clinical data 210 refers to data that may be garnered from a clinical experiment or study that establishes parameters, ranges and/or normal values that are then used as a benchmark to measure other tested subjects. The clinical data may refer to clinical values or ranges for certain variables, such as PTGi, PTGVLFi, and PTGr—defined in greater detail below, from a tested group. In one alternative, clinical data 210 may also represent one or more ranges of values for one variable or attribute. For example, clinical data for PTGi may indicate a range of values from 20-33. In another alternative, clinical data 210 may also represent multiple ranges of values. For example, clinical data for PTGi may indicate a first range of values from 20-25, which indicates a normal range; a second range of values from 25-31, which indicates a borderline range; and a third range of values from 31 and above, which indicates an abnormal range.

Predefined values 212 may refer to predefined values (for variables PTGTP, PTGi and PTGVLFi—for example) that, according to research or empirical data, correspond to certain diseases, including insulin resistance, diabetes, cardiovascular disease and autonomic neuropathy. Thus, a given value of 33 for PTGTP, for example, may correspond to diabetes.

The method 300 begins in earnest with the first step 302 wherein a patient 110 may visit a healthcare professional or doctor. During the visit, which may be a conventional, in-person visit or a virtual visit using teleconferencing technology, the doctor, and/or another healthcare professional working under the direction of the doctor, may interact with the patient 110 in order to evaluate the patient medically.

The healthcare professional may attach the at least one sensor 112 to the patient and during the visit, in step 304, certain information is generated and entered into the database 104 of server 102 as a patient record associated with patient 110. Said information may include a photoplethysmogram (PTG) 202 (garnered by a pulse oximeter), galvanic skin response data 204 (garnered by a galvanic skin response device), bioimpedance data 206 (garnered from a bioimpedance measuring device) and blood pressure data 208 (garnered from a blood pressure measuring device).

A photoplethysmogram (PTG) is an optically obtained plethysmogram, a volumetric measurement of an organ. A PTG is often obtained by using a pulse oximeter which illuminates the skin and measures changes in light absorption. PTG uses transmitted infrared and red light to measure relative blood volume in the fingertip. PTG waveforms are reflective of blood movement in cutaneous vessels and can be used to identify synchronous depolarization of cardiovascular tissue. The fundamental frequency of the PTG waveform, typically around 1 Hz reflects the heart rate. Lower frequency components such as respiratory, thermoregulatory and sympathetic nervous system effects are also contained within the PTG signal.

Figure 4A:
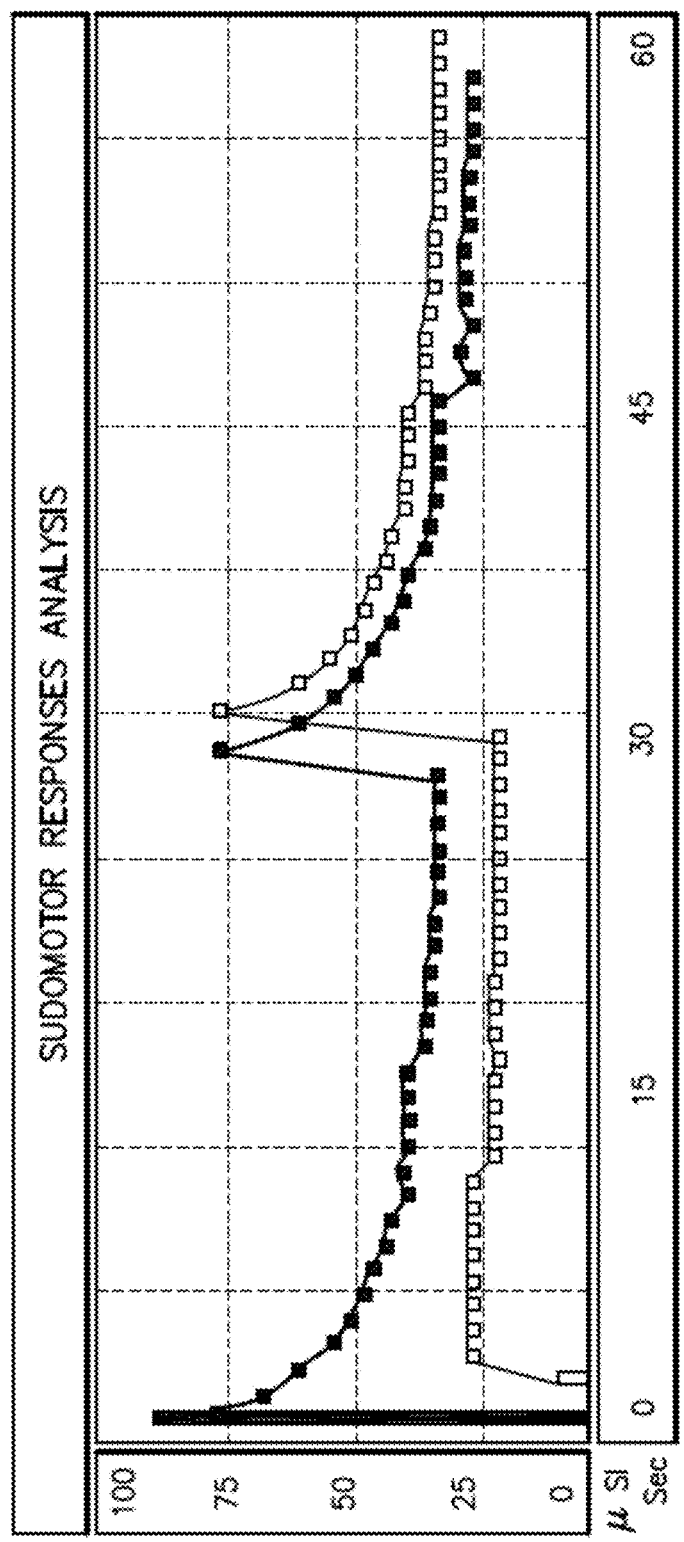
FIGS. 4A-4G are graphs showing data values collected from a patient and used for calculating a homeostatic risk score in a patient, according to an example embodiment.
Figure 4B:
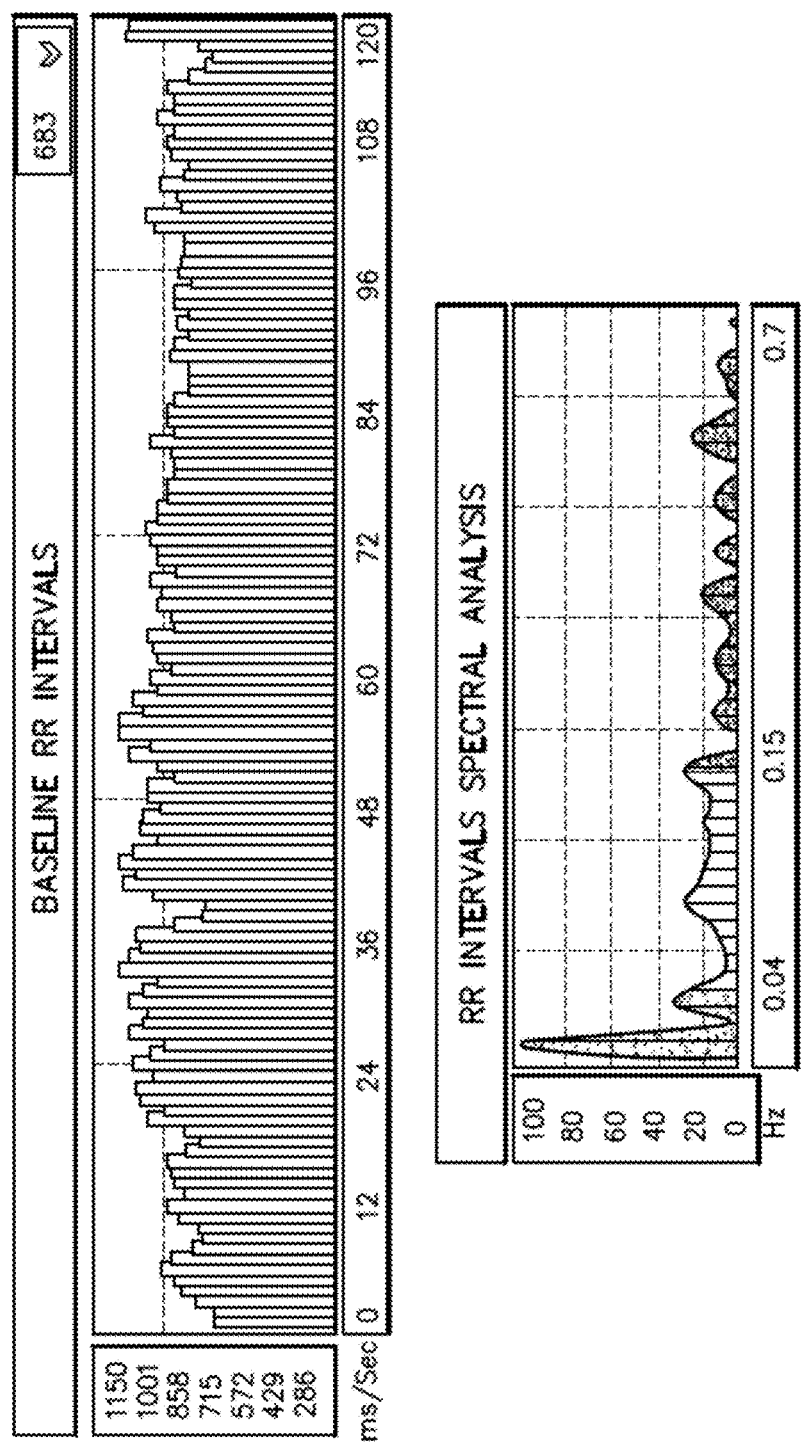

FIG. 4B shows a first graph that plots the R-wave to R-wave intervals data (the heart rate variability) over time, as said data is collected from a pulse oximeter. FIG. 4B also shows a second graph that plots the occurrence of R-wave to R-wave intervals (the heart rate variability) according to frequency, as said data is collected from a pulse oximeter.

Figure 4C:
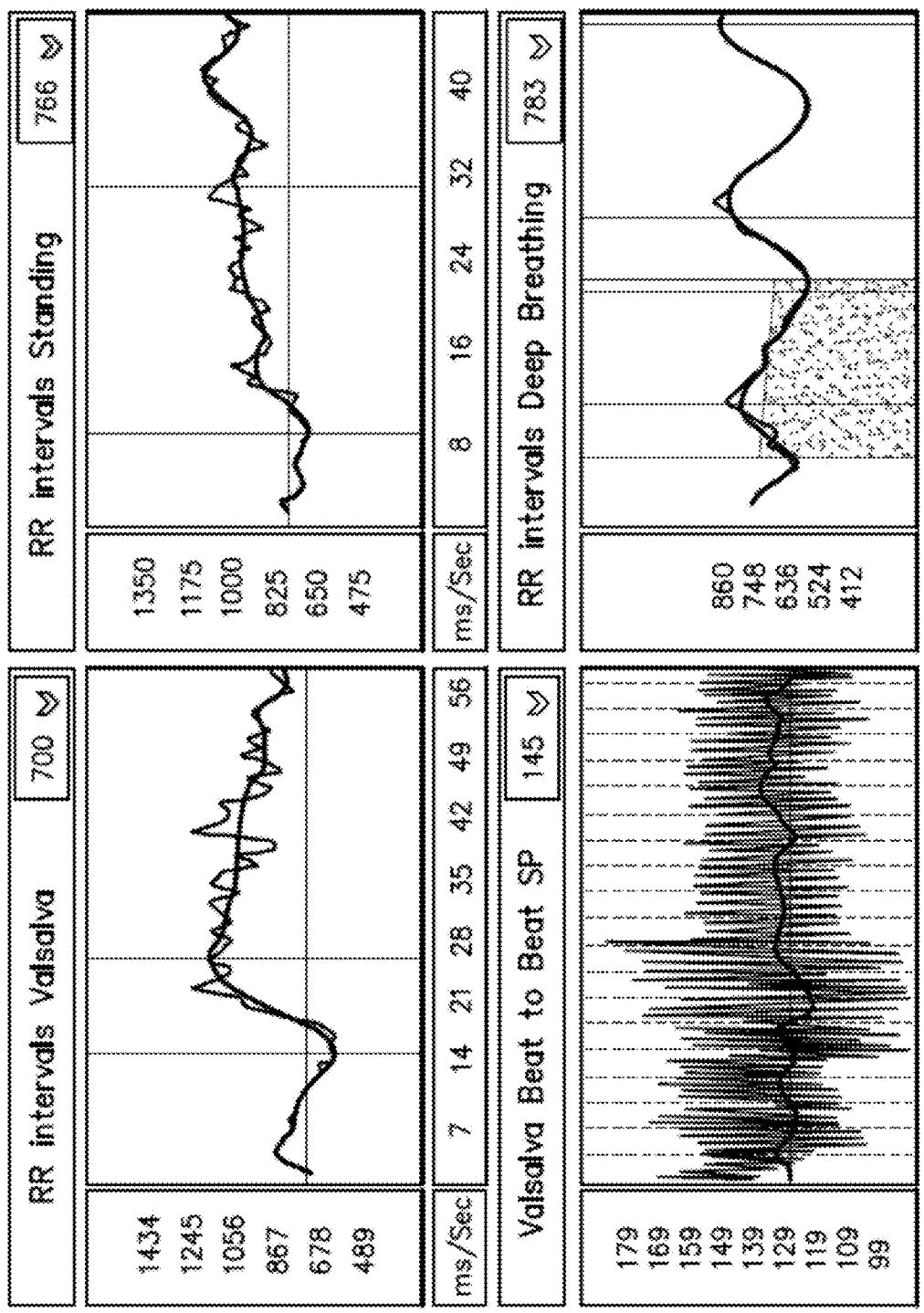

FIG. 4C shows several graphs related to a PTG taken during Ewing tests. FIG. 4C shows a first graph (at the top left) that plots the R-wave to R-wave intervals data over time, during a Valsalva maneuver (which is well known in the art), as said data is collected from a pulse oximeter. The Valsalva maneuver is performed by moderately forceful attempted exhalation against a closed airway, usually done by closing one's mouth, pinching one's nose shut while pressing out as if blowing up a balloon. FIG. 4C also shows a second graph (top right) that plots the occurrence of R-wave to R-wave intervals (the heart rate variability) according to frequency, while the patient is standing, as said data is collected from a pulse oximeter. FIG. 4C also shows a third graph (bottom left) that plots the occurrence of Valsalva beat to beat data, as said data is collected from a pulse oximeter. FIG. 4C also shows a fourth graph (bottom right) that plots the occurrence of R-wave to R-wave intervals (the heart rate variability), while the patient is breathing deeply, as said data is collected from a pulse oximeter.

Figure 4D:
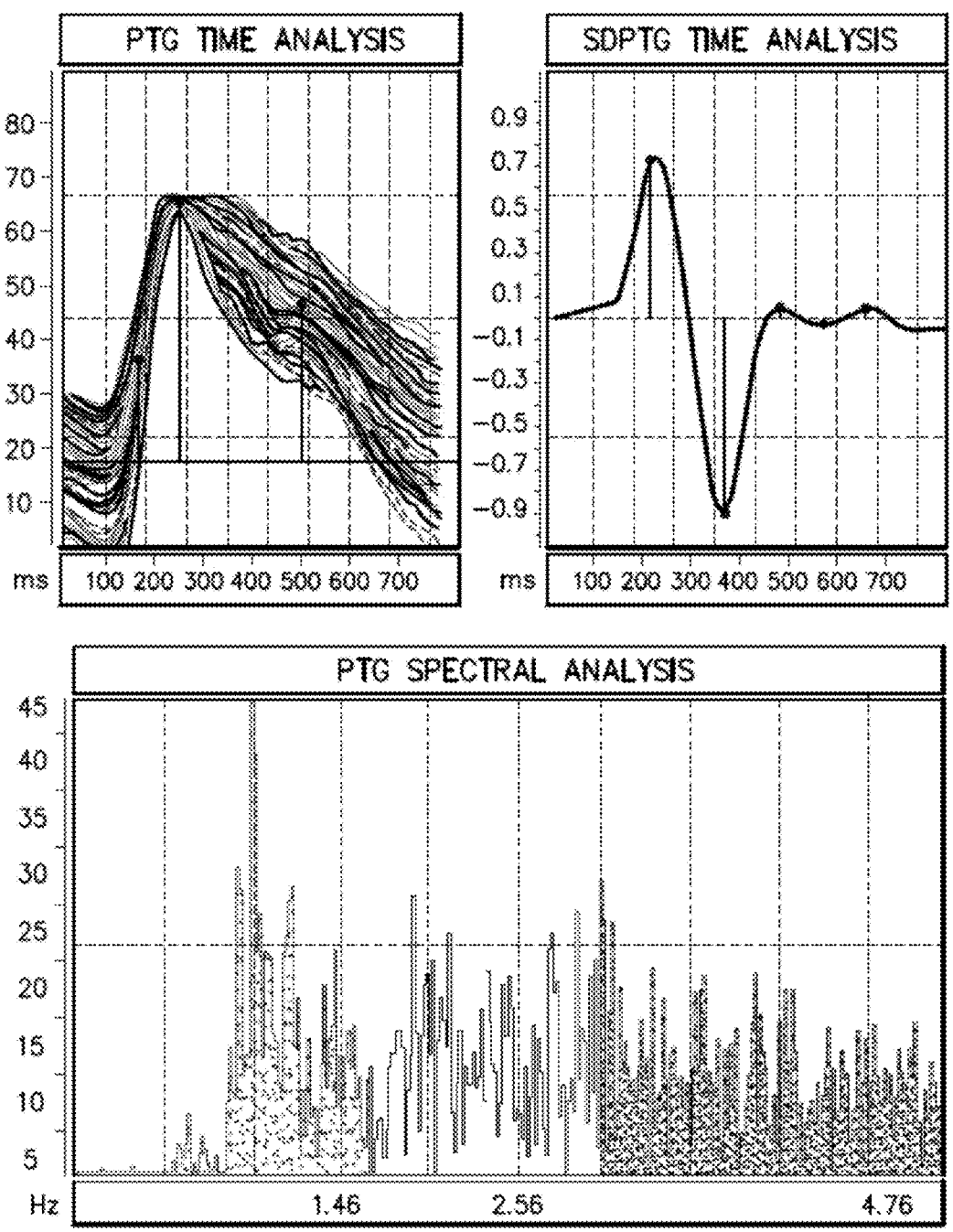
Figure 4E:
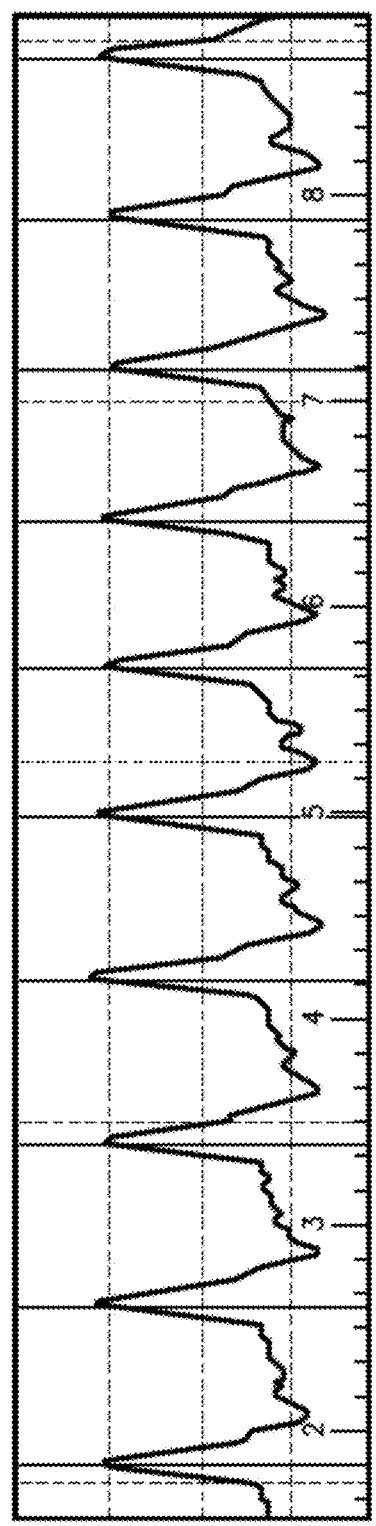
Figure 4F:
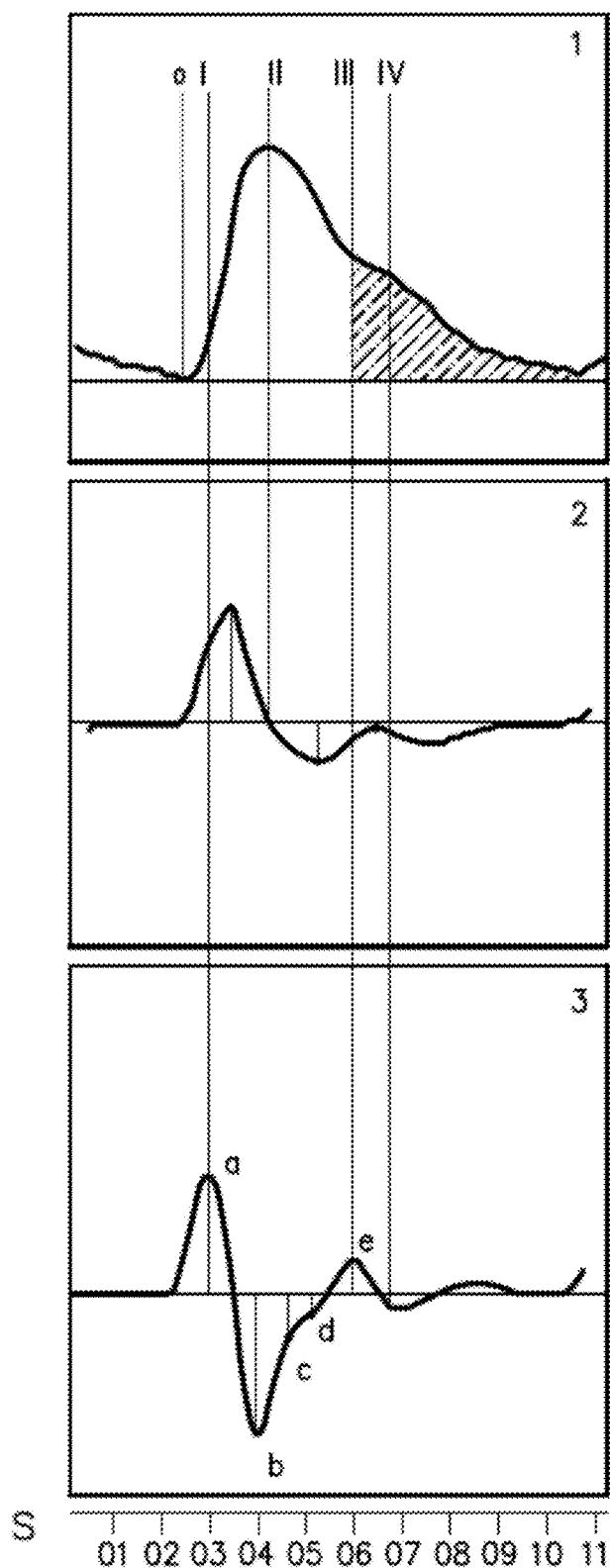
Figure 4G:
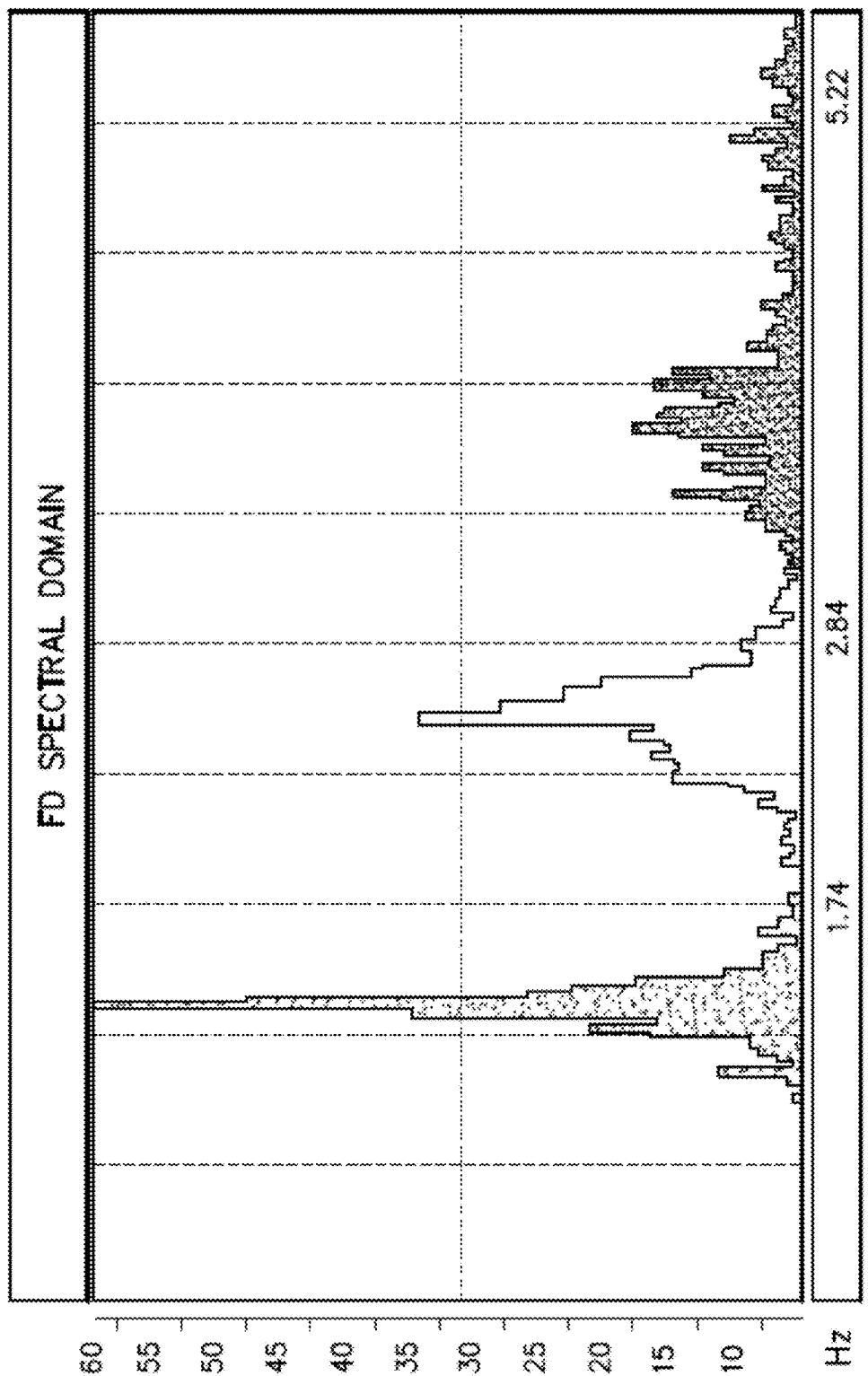
Figure 5:
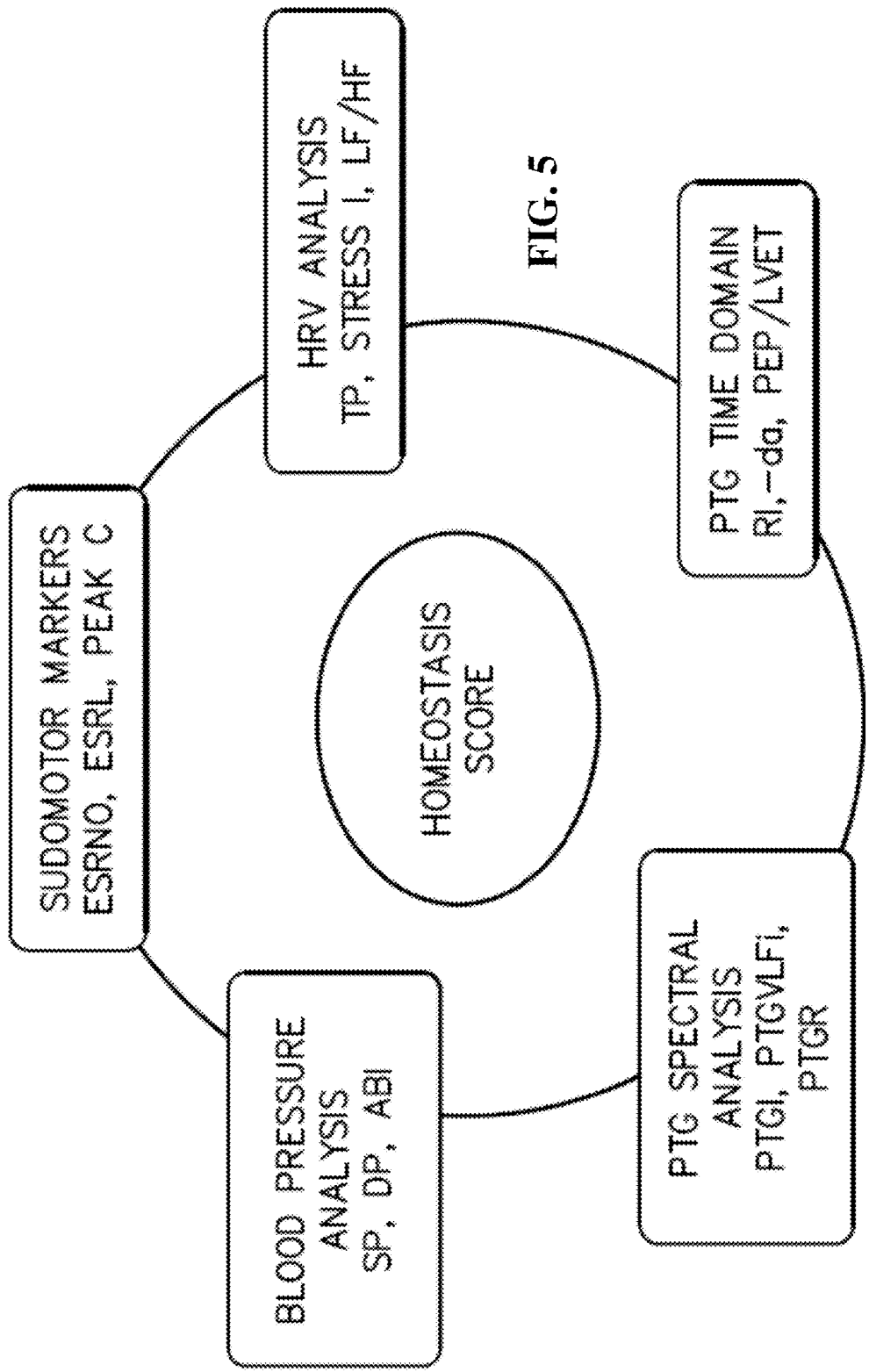
FIG. 5 is a block diagram showing the various components of data used to calculated a homeostatic risk score in a patient, according to an example embodiment.

FIG. 4D shows a first graph (top left) that plots the PTG over time, as said data is collected from a pulse oximeter. FIG. 4D shows a second graph (top right) that plots the second derivative of the waveform of the fingertip photoplethysmogram (SDPTG) over time, as said data is collected from a pulse oximeter. FIG. 4D also shows a third graph (at the bottom) that plots the PTG according to frequency, as said data is collected from a pulse oximeter. FIG. 4E shows a shows the first derivative of a PTG waveform, as said data is collected from a pulse oximeter. Instantaneous heart rate can be derived by calculating the time between two peaks of the first derivative. FIG. 4F shows an averaged PPG wave (1 at the top) and its first derivative (2 in the middle) and second derivative (3 at the bottom), as said data is collected from a pulse oximeter. FIG. 4G shows the result of a Fast-Fourier-Transform of a photoplethysmograph waveform. The waveform in the frequency domain is separated into three frequency bands: the 'very low frequency', the 'low frequency', and the 'high frequency'.

Galvanic skin response is the property of the human body that causes continuous variation in the electrical characteristics of the skin. Galvanic skin response is measured by a galvanic skin response sensor or device that measures the electrical conductance (or skin resistance) of the skin. Galvanic skin response may be represented by a value measured in micro Siemens, for example. The galvanic skin response device evaluates the segmental and general conductance of the human body with direct current via at least 2 to 6 tactile electrodes. The signal processing analysis of the measurement provides sudomotor function assessment which is related to the function of the sympathetic cholinergic division of the ANS. FIG. 4A shows a graph that plots the sudomotor response data over time, as said data is collected from a galvanic skin response device.

Bioimpedance data may be measured using a device that performs bioelectrical impedance analysis, which is a commonly used method for estimating body composition, and in particular body fat. The device actually determines the electrical impedance, or opposition to the flow of an electric current through body tissues which can then be used to calculate an estimate of total body water, body mass index (BMI), fat mass and total mass. Bioimpedance may be measured in tetra polar mode, for example. A blood pressure measuring device may be a sphygmomanometer, blood pressure meter, blood pressure monitor or blood pressure gauge device used to measure blood pressure, often composed of an inflatable cuff to collapse and then release the artery under the cuff in a controlled manner, and may include a mercury or mechanical manometer to measure the pressure. The bioimpedance device may operate in tetra polar mode to evaluate the resistance and the reactance of the human body using a mono frequency (50 KHz) via 4 tactile electrodes, to estimate body composition parameters (total body water, fat free mass, fat mass) according to predictive equations as commonly seen in peer reviews.

In step 306, the device 102 executes a spectral analysis (PTG spectral analysis) on the PTG using Fast Fourier Transform (FFT), thereby generating three constituent frequencies: PTG high frequency (PTGHF), PTG low frequency (PTGLF) and PTG very low frequency (PTGVLF) based on the PTG. A fast Fourier transform (FFT) algorithm computes the discrete Fourier transform (DFT) of a sequence, or its inverse. Fourier analysis converts a signal from its original domain (often time or space) to a representation in the frequency domain and vice versa. Specifically, in this scenario, the FFT transforms the PTG of 202 into three constituent frequencies, the high frequency, low frequency and very low frequency. The PTGHF may be a band between 0.15 and 0.6 Hz, the PTGLF may be a band ranging from 0.04 to 0.15 Hz, and the PTGVLF may be a band lower than 0.04 Hz. The FFT may use as a reference the heart rate with frequency values fixed at 1 Hertz at heart rate 60 bpm. Note that three constituent frequencies generated in this step also comprise amplitudes, which are used later in the method 300.

In step 308, the device 102 calculates multiple variables. For example, the device 102 calculates PTG Total Power (PTGTP) as the sum of PTGHF, PTGLF, and PTGVLF. In one embodiment, the FFT may be performed on the first derivative of total record of the PTG trace and calculate PTGTP in milliseconds squared. Further, the device 102 calculates PTG index (PTGi) of the spectral analysis as a sum of amplitudes of the PTGHF, PTGLF, and PTGVLF. Also, the device 102 calculates PTG VLF index (PTGVLFi) of the spectral analysis as PTGVLF divided by a value representing the galvanic skin response, measured in micro Siemens, for example. Finally, in this step, the device 102 calculates PTG ratio (PTGr) of the spectral analysis as PTGVLF divided by PTGi.

In step 308, device 102 may also calculate a heart rate variability based on the PTG and calculate a stress index based on the heart rate variability. Heart rate variability (HRV) is the physiological phenomenon of variation in the time interval between heartbeats. It is measured by the variation in the beat-to-beat interval. The stress index represents the body's adaptability to internal and external stressors that are placed on the body every day, the function of the autonomic nervous system, the level of stress the body is experiencing at the present time, and/or the fatigue or activity level of the body from a cellular level. HRV and stress index may be measured using processes that are well known in the art.

In step 308, device 102 may also calculate −da, reflection index (RI), left ventricular ejection time (LVET) and pre-ejection period (PEP) based on the PTG. The RI is a measure of small artery stiffness, and the LVET is the time measured clinically from onset to incisural notch of the carotid or other pulse; properly, the time of ejection of blood from the left ventricle beginning with aortic valve opening and ending with aortic valve closure. The PEP is the period between when the ventricular contraction occurs and the semilunar valves open and blood ejection into the aorta commences. The −da, RI, LVET and PEP may be measured using processes that are well known in the art. −da, RI, LVET and PEP may be measured using processes that are well known in the art. −da may be calculated as follows: from the second derivative of the PTG, the high of the point "d" to the horizontal line divided by the high of the point "a" to the horizontal line. See the bottom figure numbered 3 in FIG. 4F for the description of points, a, b, c and d in the second derivative of the PTG.

In step 308, device 102 may also calculate electro skin response nitric oxide (ESRNO), electro skin response latency (ESRL) and Peak C based on the galvanic skin response. ESRNO is a measured response triggered by an electrical stimulation provoking an electrochemical reaction on the bulk of patient-attached electrodes, measured as electro-conductance response nitric oxide, which corresponds to the skin microcirculation, and electro-conductance response chloride, which corresponds to sweat gland density. Peak C is peak conductance after the change in polarity in the galvanic skin response measuring device. ESRL is the measured time from the change in polarity to the Peak C at the left electrode. ESRNO, ESRL, and Peak C may be measured using processes that are well known in the art.

The galvanic skin response device may operate in the following manner. The device generates a constant low-voltage output (between 1 and 4 Volts) with a weak direct current (DC) current that is fed to the active electrode and then delivered to the contralateral electrode in two directions for each pathway. The polarity of the contralateral electrode affects which ions are attracted and repelled, which either prevents or allows the output of ions through the sweat gland ducts. Three markers measuring the electrochemical reactions on the bulk of electrodes may be measured: 1) peak conductance after the change in polarity (Peak C); 2) conductance at the cathode related to the water reduction; and 3) conductance at the anode related to the water and negative ions oxidation. During the measurement process, the polarity is alternated, which provokes an increase of heat, as well as the delivered voltage to the contralateral electrode in the tissue surrounding the sweat glands, and mediate a peak of conductance. Because the heat and increased voltage induce a vasodilation of surrounding vessels, the resulting hyperemia increases skin temperature and thus sets up the sweat response.

In step 308, device 102 may also calculate body mass index (BMI) and fat mass based on the bioimpedance. BMI and fat mass may be measured using processes that are well known in the art. In step 308, device 102 may also calculate systolic pressure, diastolic pressure and ankle-brachial index (ABI) based on the blood pressure. Ankle Brachial Index (ABI) is the systolic pressure at the ankle, divided by the systolic pressure at the arm. Systolic pressure, diastolic pressure and ABI may be measured using processes that are well known in the art.

In step 310, the device 102 may calculate a first score based on PTGTP, stress index, PTGLF, PTGHF, RI, −da, PEP, LVET, PTGi, PTGVLFi, and PTGr. Specifically, the first score may be based on an HRV score and a PTG score.

The HRV score (HRV Analysis) is based on PTGTP, stress index (Stress I), PTGLF (LF), PTGHF (HF). In one embodiment, the device 102 calculates the HRV score in the following manner device 102 compares the calculated values for PTGTP, stress index (Stress I), PTGLF, PTGHF to clinical data 210 to determine how the values compare. The comparison results in numerical values that are used to calculate the HRV score. The numerical values of the comparison are calculated as follows.

The comparison of this step results in data being stored, wherein said data represents the results of the comparison. For example, a PTGi value of 23 is compared to a clinical data 210, which shows a PTGi value of 33. Thus, in this example, the method 300 stores a data structure, or a numerical value (such as −1), that indicates that the generated PTGi value of 23 is less than the clinical PTGi value of 33. If the generated PTGi value was 33, the method 300 may store a data structure, or a numerical value (such as 0), that indicates that the generated PTGi value of 33 is equal to the clinical PTGi value of 33. If the generated PTGi value was 36, the method 300 may store a data structure, or a numerical value (such as +1), that indicates that the generated PTGi value of 33 is greater than the clinical PTGi value of 33.

In another example, clinical data for PTGi may indicate a range of values from 20-33. Thus, in this example, the method 300 stores a data structure, or a numerical value (such as −1) that indicates that a generated PTGi value of 19 is less than the clinical PTGi range of values. If the generated PTGi value was 25, the method 300 may store a data structure, or a numerical value (such as 0), that indicates that the generated PTGi value of 25 is within the clinical PTGi range of values. If the generated PTGi value was 35, the method 300 may store a data structure, or a numerical value (such as +1), that indicates that the generated PTGi value of 35 is greater than the clinical PTGi range of values.

In another example, clinical data 210 may also represent multiple ranges of values, wherein each range is associated with a superlative or degree. For example, clinical data for PTGi may indicate a first range of values from 20-25, which indicates a normal range; a second range of values from 26-31, which indicates a borderline range; and a third range of values from 32 and above, which indicates an abnormal range. Thus, in this example, the method 300 stores a data structure, or a numerical value (such as 2) that indicates that a generated PTGi value of 22 is within the clinical PTGi range of values of the normal range. If the generated PTGi value was 26, the method 300 may store a data structure, or a numerical value (such as 1), that indicates that the generated PTGi value of 26 is within the clinical PTGi range of values of the borderline range. If the generated PTGi value was 35, the method 300 may store a data structure, or a numerical value (such as 0), that indicates that the generated PTGi value of 35 is within the clinical PTGi range of values for the abnormal range.

In the later example above, the device 102 stores all numerical values that resulted from the comparison of the calculated values of the patient (calculated above) to stored clinical data 210. Also, device 102 may sum the numerical values garnered from the comparison of each of the values to clinical data, in order to calculate the HRV score.

The PTG score (PTF time domain analysis) is based on RI, −da, PEP, LVET, PTGi, PTGVLFi, and PTGr. In one embodiment, the device 102 calculates the PTG score in the following manner device 102 compares the calculated values for RI, −da, PEP, LVET, PTGi, PTGVLFi, and PTGr to clinical data 210 to determine how the values compare. The comparison results in numerical values that are used to calculate the PTG score (see above for a description of this process, as is applies to the calculation of the HRV score). From the second derivative of the PTG, the high of the point "d" to the horizontal line divided by the high of the point "a" to the horizontal line represents the ratio "negative da," also known as "-da". See the bottom figure numbered 3 in FIG. 4F for the description of points, a, b, c and d in the second derivative of the PTG.

The first score may be based on the HRV score and the PTG score. Specifically, the first score may be a sum of the HRV score and the PTG score.

In step 310, the device 102 may calculate a second score based on the ESRNO, ESRL and the Peak C. The second score (sudomotor markers analysis) may be referred to as the galvanic skin response score or the sudomotor score. In one embodiment, the device 102 calculates the second score in the following manner device 102 compares the calculated values for ESRNO, ESRL and the Peak C to clinical data 210 to determine how the values compare. The comparison results in numerical values that are used to calculate the second score.

In step 310, the device 102 may calculate a third score based on the BMI and fat mass. The third score may be referred to as the bioimpedance score or the body composition score. In one embodiment, the device 102 calculates the third score in the following manner: device 102 compares the calculated values for BMI and fat mass (FM) to clinical data 210 to determine how the values compare. The comparison results in numerical values that are used to calculate the third score. In another embodiment, the device 102 calculates the third score in the following manner if the BMI and FM are in the normal range, then a score of 5 is given; if the BMI and FM are a second range, then a score of 4 is given; if the BMI and FM are in a third range, then a score of 3 is given; if the BMI and FM are in a fourth range, then a score of 2 is given; if the BMI and FM are above a certain value, then a score of 1 is given.

In step 310, the device 102 may calculate a fourth score based on the systolic pressure, diastolic pressure and ABI. The fourth score may be referred to as the BP or blood pressure score. In one embodiment, the device 102 calculates the fourth score (blood pressure analysis) in the following manner device 102 compares the calculated values for systolic pressure (SP), diastolic pressure (DP) and ABI to clinical data 210 to determine how the values compare. The comparison results in numerical values that are used to calculate the fourth score.

In one embodiment, the device 102 calculates the fourth score (blood pressure analysis) in the following manner if SP<=120, and DP<=80, then a score of 4 is given; if SP<=121-139, and DP<=81-89, then a score of 3 is given; if SP<=140-159 and/or DP<=90-99, then a score of 2 is given; if SP<=>160 and/or SP>100, then a score of 1 is given; if ABI>1 and <1, then a score of 0 is given; if ABI<0.9 and >0.6, then a score of 1 is given; if ABI<=0.6, then a score of 2 is given, and ABI>=1.40, then a score of 3 is given.

In step 312, the device 102, calculates a homeostatic risk score based on the first, second, third and fourth scores calculated above. Following is an example formula used to calculate the homeostatic risk score: calculate the sum of the first, second, third and fourth scores calculated above. The homeostatic risk score corresponds to the patient's risk associated with said metabolic diseases, and their complications, as well as the treatment of said diseases. The homeostatic risk score provides a quick and accurate overview of a patient's homeostasis processes and responses, using key indicators, to understand the patient's potential adaptation to lifestyle, disorders, diseases and any current treatments.

Finally, in step 314, device 102 displays the homeostatic risk score. Alternatively, device 102 transmits the homeostatic risk score over the network 106 to another computing device for storage and/or display on said other device.

EXPERIMENTAL DATA

The claimed subject matter is supported by various clinical trials as described in the specific examples below. In a first study, a cross-sectional assessment to detect type 2 diabetes with endothelial and autonomic nervous system markers using a novel system was undertaken. The background of the first study was as follows. Type 2 diabetes mellitus is frequently unrecognized until complications appear. Diabetic autonomic neuropathy is one of the early complications of type 2 diabetes mellitus, resulting in autonomic nervous system (ANS) dysfunction. The purpose of this study was to determine the validity of ANS function indicators to screen for type 2 diabetes mellitus, as measured by the TM-Oxi and SudoPath system.

The method of the first study were as follows. All enrolled participants completed a basic sociodemographic and medical history questionnaire including current medications. Healthy controls (n=25) underwent a 2-hour oral glucose tolerance test (OGTT) to evaluate glucose, insulin, and insulin C-peptide. Patients with type 2 diabetes mellitus (n=24) were assessed with fasting plasma glucose (FPG) and glycosylated hemoglobin. The TM-Oxi and SudoPath system evaluation was completed by all subjects. Data were analyzed using SPSS 22. Frequency and descriptive statistics were calculated on all variables. The criterion for statistical significance was $\alpha=0.05$.

The results of the first study were as follows. The twenty-five healthy controls had a mean age of 37.0 years. The twenty-four type 2 diabetes mellitus patients currently undergoing standard treatment had a mean age of 48.9 years. Based on the American Diabetes Association guidelines, we detected pre-diabetes in 4 subjects and diabetes in 1 subject, while all other subjects had normal FPG values. At 120 minutes, the correlations between the OGTT and cardiometabolic risk score (CMRS) were: $r=0.56$ ($p=0.004$) for glucose and $r=0.53$ ($p=0.006$) for insulin. At 120 minutes, the correlations between the OGTT and photoplethysmography index (PTGi) were: $r=-0.56$ ($p=0.003$) for glucose and $r=-0.41$ ($p=0.04$) for insulin. The CMRS, PTGi, and plethysmography total power index (PTGVLFi) differed significantly between the diabetes patients and healthy participants. The specificity and sensitivity for the CMRS, PTGi, and PTGVLFi comparing the diabetes patients with healthy controls were high.

The conclusions of the first study were as follows. The TM-Oxi and SudoPath system shows promise as a valid, convenient, and non-invasive screening method for type 2 diabetes mellitus. The ANS function and CMR indicators measured by this system may be useful in guiding diabetes and cardiovascular health screening, treatment, and monitoring.

In a second study, a spectral analysis of photoplethysmography to evaluate an independent cardiovascular risk factor was undertaken. The background of the second study was as follows. In this study, the researches evaluated homeostatic markers correlated to autonomic nervous and endothelial functions in a population of coronary artery disease (CAD) patients versus a control group. Since CAD is the highest risk marker for sudden cardiac death, the study objective is to determine whether an independent cardiovascular risk score based on these markers can be used alongside known conventional cardiovascular risk markers to strengthen the understanding of a patient's vascular state.

The materials and methods of the second study were as follows. Sixty-five subjects (13 women) with a mean age of 62.9 years (range 40-80 years) who were diagnosed with CAD using coronary angiography (group 1) and seventy-two subjects (29 women) with a mean age of 45.1 years (range 18-85 years) who claimed they were healthy (group 2) were included in the study. These subjects underwent examination with the TM-Oxi and SudoPath systems at IPC Heart Care Centers in Mumbai, India. The TM-Oxi system takes measurements from a blood pressure device and a pulse oximeter. The SudoPath measures galvanic skin response to assess the sudomotor pathway function. Spectral analysis of the photoplethysmograph (PTG) waveform and electrochemical galvanic skin response allow the TM-Oxi and SudoPath systems to calculate several homeostatic markers, such as the PTG index (PTGi), PTG very low frequency index (PTGVLFi), and PTG ratio (PTGr). The focus of this study was to evaluate these markers (PTGi, PTGVLFi, and PTGr) in CAD patients against a control group, and to calculate an independent cardiovascular risk factor score: the PTG cardiovascular disease risk score (PTG CVD), calculated solely from these markers. We compared PTGi, PTGVLFi, PTGr, and PTG CVD scores between the CAD patient group and the healthy control group. Statistical analyses were performed using receiver operating characteristic curves to determine the specificity and sensitivity of the markers to detect CAD at optimal cutoff values for PTGi, PTGVLFi, PTGr, and PTG CVD. In addition, correlation analyses between these markers and conventional autonomic nervous system and endothelial function markers were performed to understand the possible underlying physiological sources of the differences observed in marker values between CAD patients and healthy control patients. Additionally, t-tests were performed between two subgroups of the CAD patient group to determine whether diabetic or coronary artery bypass grafting (CABG) patients have significantly different PTGi marker values.

The results of the second study were as follows. Each spectral analysis PTG marker yielded a high specificity and sensitivity to detect CAD. Most notably, the PTG CVD score had a sensitivity of 82.5% and specificity of 96.8%, at a cutoff of 2, when used to detect CAD (P=0.0001; area under the receiver operating characteristic curve=0.967). The PTG spectral analysis markers were well-correlated to other autonomic nervous system and endothelial function markers. CAD diabetic patients (n=27) had a lower PTGi value compared with the CAD non-diabetic patients (n=38): and patients that underwent CAB G (n=18) had a higher PTGi value compared with the CAD without CABG surgery patients (n=47).

The conclusions of the second study were as follows. The spectral analysis of the photoplethysmography method is noninvasive, fast, operator-independent, and cost-effective, as only an oximeter and a galvanic skin response device are required in order to assess in a single testing the autonomic nervous system and endothelial function. The spectral analysis techniques used on the photoplethysmogram, as outlined in this study, could be useful when used alongside conventional known cardiovascular tests.

Figure 6:
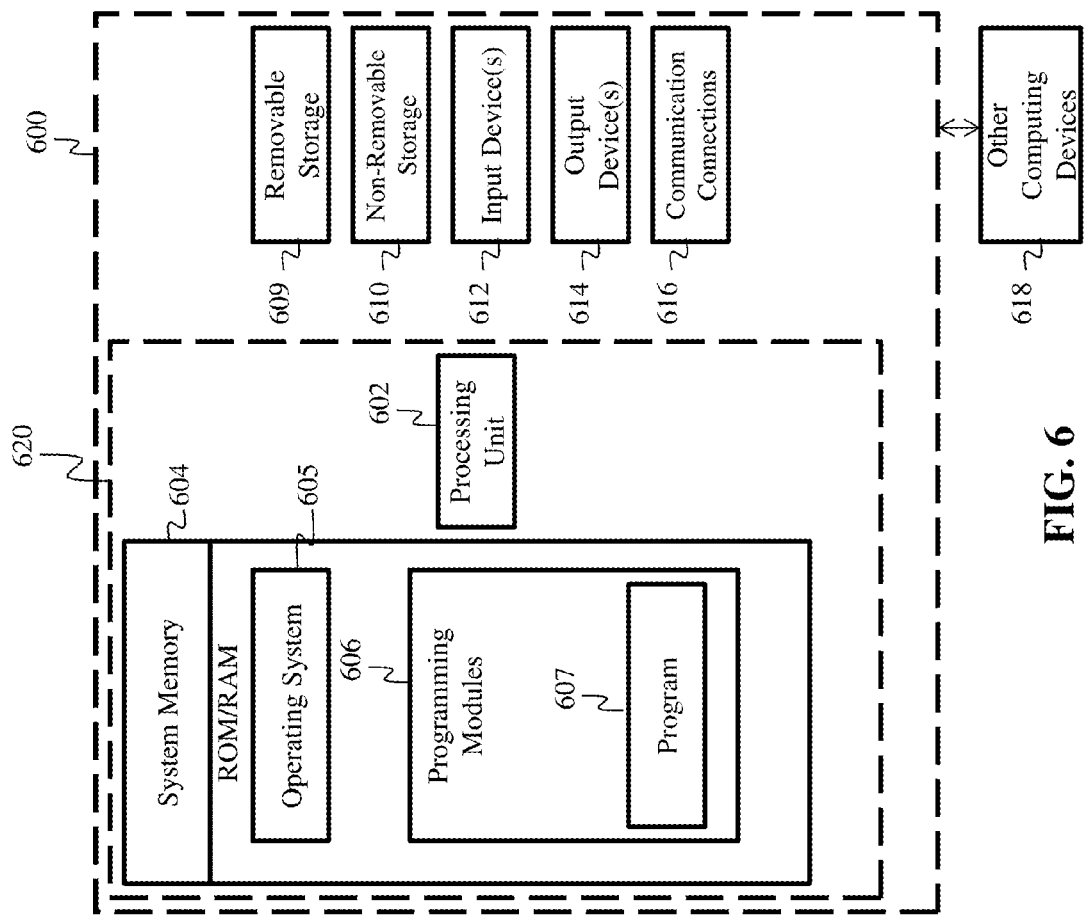
FIG. 6 is a block diagram of a system including a computing device, according to an example embodiment.

FIG. 6 is a block diagram of a system including an example computing device 600 and other computing devices. Consistent with the embodiments described herein, the aforementioned actions performed by servers/computers 102, 112, 140 may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for method 300 as described above. Method 300 may operate in other environments and is not limited to computing device 600.

With reference to FIG. 6, a system consistent with an embodiment may include a plurality of computing devices, such as computing device 600. In a basic configuration, computing device 600 may include at least one processing unit 602 and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of 102, 112, and 140. Furthermore, embodiments may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of device 600. Computing device 600 may also have input device(s) 612 such as a keyboard, a mouse, a pen, a sound input device, a camera, a touch input device, etc. Output device(s) 614 such as a display, speakers, a printer, etc. may also be included. The aforementioned devices are only examples, and other devices may be added or substituted.

Computing device 600 may also contain a communication connection 616 that may allow device 600 to communicate with other computing devices 618, such as over a network in a distributed computing environment, for example, an intranet or the Internet. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g. program module 607) may perform processes including, for example, one or more of method 400's stages as described above. The aforementioned processes are examples, and processing unit 602 may perform other processes. Other programming modules that may be used in accordance with embodiments may include electronic mail and contacts applications, word processing applications, spreadsheet applications, database applications, slide presentation applications, drawing or computer-aided application programs, etc.

Generally, consistent with the embodiments, program modules may include routines, programs, components, data structures, and other types of structures that may perform particular tasks or that may implement particular abstract data types. Moreover, embodiments may be practiced with other computer system configurations, including hand-held devices, multiprocessor systems, microprocessor-based or programmable consumer electronics, minicomputers, mainframe computers, and the like. Embodiments may also be practiced in distributed computing environments where tasks are performed by remote processing devices that are linked through a communications network. In a distributed computing environment, program modules may be located in both local and remote memory storage devices.

Furthermore, embodiments may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments may also be practiced using other technologies capable of performing logical operations such as, for example, AND, OR, and NOT, including but not limited to mechanical, optical, fluidic, and quantum technologies. In addition, embodiments may be practiced within a general purpose computer or in any other circuits or systems.

Galvanic skin response measurements are typically made with weak direct current between two tactile electrodes placed symmetrically on skin with the higher density of sweat glands of the subject (i.e. palm of hands, sole of feet or forehead). The hand and foot electrodes are typically at least 250 cm$^2$ and in stainless steel or at least 37 cm$^2$ in AgAgCl or cloth disposable electrodes. The forehead electrodes are typically disposable (single use) and preferably in AgAgCl. Each electrode is alternatively cathode then anode (change in voltage polarity), which permits in the particular embodiment described the recording of the intensity/voltage/resistance and conductance (Law of Ohm) of each pathway (volume of the body between 2 electrodes) of the human body. The galvanic skin response generates positive (over the ground) and negative (below ground) voltage. From left to right electrodes, the voltage is negative and from right to left electrodes, the voltage is positive. The galvanic skin response measurement process is an improved sympathetic skin response method following a constant electrical stimulation, and change of the measured electrode at the middle of the measurement with the following sequence:

Right to left foot 15 seconds and measurement of the voltage of the left foot electrode/change in measured electrode 15 seconds and measurement of the right foot electrode.

Right to left hand 15 seconds and measurement of the voltage of the left hand electrode/change in measured electrode 15 seconds and measurement of the right hand electrode.

Left to right foot 15 seconds and measurement of the voltage of the right foot electrode/change in measured electrode 15 seconds and measurement of the left foot electrode.

Left to right hand 15 seconds and measurement of the voltage of the right hand electrode/change in measured electrode 15 seconds and measurement of the left hand electrode.

The change in direction of the voltage provides an increased difference of potential (voltage) of peak of voltage (negative+positive output voltage on the bulk of the electrodes). Galvanic skin response measurements provide a quantitative evaluation of the sweat response according to the electrochemical oxidation measurements on the bulk of the left electrodes and according to the carried energy in electric fields on the right electrodes (when the negative voltage is applied, the electrical measurement is not generated by electrons or ions). Since sweat is a dilute sodium chloride (NaCl) solution, and a constant weak direct current of 1.28 V is sent between 2 electrodes, the general principle of Electrolysis of Aqueous NaCl is applicable. Sweat comprises 99.2 to 99.6% of water and 0.2 to 0.5% of NaCl. The electrochemical window is defined by both reduction and oxidation according to the following reactions: at the right electrodes, the output voltage is negative, the electrical measurement is not generated by ions, therefore we get only a release of water ($H_2O$ has a reduction potential of $-0.83$ V).

The measured electrochemical reduction half reaction related to the sweat production occurring at the cathode is: $2H_2O+(2e-)\rightarrow H_2 (g)+(2OH-)$ when the output voltage at the passive responding electrode is $<=-0.83V$ which is corresponding to 65 µSi. And consequently produces hydrogen gas and OH– ions.

The measured conductance (average of maximum conductance and conductance at 15 second after the maximum) at the right electrodes is named ESR NO (Electro Skin response—Nitric Oxide) because no ions are released and therefore the reaction is only related to the vasodilation response of surrounding vessel induced by the electrical stimulation we suggest the more probable assumption that ESRNO could be a valid marker of the microcirculatory state and it is our first marker of the sudomotor function. ESRNO <65 µSi is considered as lower sweat response and could be a sign microcirculatory disorder.

At the left electrodes the output voltage is positive. Cl— ions could not be oxidized at the positive electrode for 2 reasons: a) the voltage applied is not thermodynamically sufficient to drive electrolysis (Cl— ions have an oxidation potential of 1.39V and the generator produces 1.28V), b) there is a competition between the negative ions at the positive anode. The Cl— ions compete with the hydroxide (OH—) ions to release their electrons to the anode. Regarding the very low concentration of chloride ions in the sweat (0.2 to 0.5%), and very high concentration of OH— ions from the water electrolysis, only, OH— are released at the anode. OH— has an oxidation potential of 0.40 V and H2O has an oxidation potential of 1.23 V. The measured electrochemical oxidation half reactions occurring at the anode are:

4OH— → 2H2O+O2 (g)+4e− when the output voltage at the passive responding electrode is >=0.40V which is corresponding to 37 µSi 2 H2O→O2 (g)+4 H++4 e− when the output voltage at the passive responding electrode is >=1.23V which is corresponding to 90 µSi And consequently produce water, oxygen gas and H+ ions.

We identified the following at the left electrode two markers: a) the Peak conductance at the left electrode is the main marker of the sudomotor function, b) the change in voltage direction increases the output voltage according to the patient skin resistance, and therefore provides a peak of conductance (Peak C), c) the measured voltage of the responding passive left electrode <0.40 V (37 µSi) is a marker of absence of sweat response at the anode and significant sudomotor dysfunction, d) the measured voltage of the responding passive electrode left electrode <1.23V (90 µSi) and >0.40 V (37 µSi) is a marker of a reduced sweat response at the anode and sudomotor dysfunction.

With regard to oximeter signal processing analysis, one method for monitoring cardiovascular events and peripheral circulation is through photoplethysmographic (PTG) analysis. PTG uses transmitted infrared and red light to measure relative blood volume in the fingertip. PTG waveforms are reflective of blood movement in cutaneous vessels and can be used to identify synchronous depolarization of cardiovascular tissue. The fundamental frequency of the PTG waveform, typically around 1 Hz reflects the heart rate. Lower frequency components such as respiratory, thermoregulatory and sympathetic nervous system effects are also contained within the PTG signal. Arterial stiffness, indicative of endothelial dysfunction, may also be measurable from calculations made using the PTG waveforms analysis. These measurements do not require lengthy examinations and are non-invasive approaches to identify abnormal cardiovascular function, possibly stemming from ANS and endothelial dysfunction.

With regard to PTG time domain analysis, throughout the entirety of the PTG waveform, relative changes in a patient's heart rate can be extracted by calculating the peak-to-peak interval. In order to find the peak-to-peak interval with high accuracy, in this study we extracted local maximum of the first derivatives. The time between these points is defined as the peak-to-peak interval, and is calculated based on the sampling frequency and the number of samples collected between the two defined peaks. The sampling frequency of the pulse oximeter used in this study is 60 Hz.

First and second derivatives of the PTG waveform can aid in understanding a single or average PTG wave. FIG. 4F shows an averaged PTG wave (top figure numbered 1) created from several extracted waves in the full PTG waveform. By calculating the first derivative (middle figure numbered 2) and second derivative (lower figure numbered 3), one can display measurements of various cardiac events. The time between points I and the preceding trough in the top figure corresponds to an estimate of the pre-ejection period (PEP). Point I is extracted from the second derivative point a (see bottom figure numbered 3). Point III in the top figure corresponds to the dichrotic notch, separating systole (yellow) and diastole (purple) phases of the cardiac cycle and is extracted from point e in the second derivative (see bottom figure numbered 3). The time between point II and point I corresponds to estimates of the left-ventricular-ejection-time (LVET). Point IV in the top figure corresponds to the diastolic peak, extracted from the trough following point (e) in the second derivative (see bottom figure numbered 3).

Additionally, ratios of the amplitude of (a) to amplitudes of b, c, d, and e (see bottom figure numbered 3 in FIG. 4F), can aid in understanding arterial stiffness. Studies have shown that ratios lb/al and ld/al decrease in aging populations and some studies have linked these ratios directly to arterial distensibility. The ratio c/a has been linked to hypertension and has also been found to decrease with age. Ratio d/a specifically may be useful in evaluating vasoactive agents and left ventricular afterload. Takazawa et al. used an index (b−c−d−e)/a to evaluate peripheral vascular aging and noted potential use for screening atherosclerosis.

With regard to PTG spectral analysis, the Fourier transform of the PTG recording could reveal information regarding autonomic activity and heart rate variability. From this information, average heart rate, power of each frequency band, peak amplitudes and their corresponding frequency bins, and total power can be extracted. In various studies, diagnostic markers may be based off of the Fourier transformed PTG signal. Harmonic components included in the PTG waveform and elucidated through spectral analysis include those associated with heart rate variability, respiratory effects on the cardiac cycle, systolic and diastolic effects on peripheral blood flow, and the ability for cutaneous blood vessels to dilate and contract. Clinical studies showed the correlation between PTG spectral analysis markers with endothelial dysfunction as well as with the autonomic nervous system (ANS) dysfunction or failure.

Embodiments, for example, are described above with reference to block diagrams and/or operational illustrations of methods, systems, and computer program products according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for determining homeostatic risk in a patient, in order to screen metabolic diseases and/or their complications and/or their treatment management, the system comprising:

a plurality of sensors coupled with the patient, wherein the plurality of sensors includes: i) a galvanic skin response sensor that generates positive, above-ground voltage and negative, below-ground voltage and measures galvanic skin response, ii) a bioimpedance sensor for measuring bioimpedance in tetra-polar mode and a frequency of 50 KHz, iii) a pulse oximeter sensor set to a frequency of 60 Hz for measuring a photoplethysmogram (PTG) waveform with a frequency of 1 Hz, and iv) a blood pressure sensor for measuring blood pressure;

a processor communicatively coupled with the plurality of sensors, the processor configured for:

a) executing a spectral analysis on the PTG using Fast Fourier Transform computing a Discrete Fourier Transform (DFT) of a sequence with a reference heart rate having frequency values fixed at 1 Hertz at a heart rate of 60 bpm, thereby generating three constituent frequencies: PTG high frequency (PTGHF), PTG low frequency (PTGLF) and PTG very low frequency (PTGVLF) based on the PTG;

b) calculating PTG Total Power (PTGTP) as equal to PTGHF+PTGLF+PTGVLF;

c) calculating PTG index (PTGi) of the spectral analysis as equal to amplitude of PTGHF+amplitude of PTGLF+amplitude of PTGVLF;

d) calculating PTG VLF index (PTGVLFi) of the spectral analysis as equal to PTGVLF divided by a value derived from the galvanic skin response;

e) calculating PTG ratio (PTGr) of the spectral analysis as equal to PTGVLF divided by PTGi;

f) calculating a heart rate variability based on the PTG and calculating a stress index based on the heart rate variability;

g) calculating –da as equal to an amplitude of a fourth point of a second derivative of the PTG divided by an amplitude of a first point of the second derivative of the PTG, reflection index (RI), which is a measure of artery stiffness, left ventricular ejection time (LVET) as equal to a time between a global maxima of the PTG, and a dicrotic notch of the PTG, and pre-ejection period (PEP) as equal to a time between a global minima of the PTG and a global maxima of a first derivative of the PTG;

h) calculating a first score based on PTGTP, stress index, PTGLF, PTGHF, RI, –da, PEP, LVET, PTGi, PTGVLFi, and PTGr;

i) calculating electro skin response nitric oxide (ESRNO), which is a measure of an average of maximum conductance and conductance at 15 seconds after the maximum conductance at a particular electrode, Peak C, which is a maximum conductance reading, and electro skin response latency (ESRL), which is a measure of an amount of time between change of polarity of the galvanic skin response sensor and Peak C, based on the galvanic skin response;

j) calculating a second score based on the ESRNO, ESRL and the Peak C;

k) calculating body mass index (BMI) fat mass based on the bioimpedance;

l) calculating a third score based on the BMI and fat mass;

m) calculating systolic pressure, diastolic pressure and ankle-brachial index (ABI) based on the blood pressure;

n) calculating a fourth score based on the systolic pressure, diastolic pressure and ABI;

o) calculating a homeostatic risk score based on the first, second, third and fourth scores that were calculated, wherein the homeostatic risk score corresponds to the homeostatic risk of the patient; and a display for displaying the homeostatic risk score.

2. The system of claim 1, wherein the step of calculating a first score further comprises:

calculating a first component score based on based on PTGTP, stress index, PTGLF, PTGHF;

calculating a second component score based on RI, –da, PEP, LVET, PTGi, PTGVLFi, and PTGr; and calculating the first score as equal to the first component score plus the second component score.

3. The system of claim 2, wherein the step of calculating a homeostatic risk score further comprises:

calculating the homeostatic risk score as equal to the first score plus the second score plus the third score plus the fourth score.

4. A method on a computer system for determining homeostatic risk in a patient, in order to screen metabolic diseases and/or their complications and/or their treatment management, the method comprising:

a) receiving, from one or more sensors coupled with the patient, galvanic skin response, bioimpedance, a photoplethysmogram (PTG), and blood pressure from the patient;

b) executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG;

c) calculating PTG Total Power (PTGTP) as equal to PTGHF+PTGLF+PTGVLF, d) calculating PTG index (PTGi) of the spectral analysis as equal to amplitude of PTGHF+amplitude of PTGLF+amplitude of PTGVLF;

e) calculating PTG VLF index (PTGVLFi) of the spectral analysis as equal to PTGVLF divided by a value derived from the galvanic skin response;

f) calculating PTG ratio (PTGr) of the spectral analysis as equal to PTGVLF divided by PTGi;

g) calculating a heart rate variability based on the PTG and calculating a stress index based on the heart rate variability;

h) calculating –da as equal to an amplitude of a fourth point of a second derivative of the PTG divided by an amplitude of a first point of the second derivative of the PTG, reflection index (RI), which is a measure of artery stiffness, left ventricular ejection time (LVET) as equal to a time between a global maxima of the PTG, and a dicrotic notch of the PTG, and pre-ejection period (PEP) as equal to a time between a global minima of the PTG and a global maxima of a first derivative of the PTG;

i) calculating a first score based on PTGTP, stress index, PTGLF, PTGHF, RI, –da, PEP, LVET, PTGi, PTGVLFi, and PTGr;

j) calculating electro skin response nitric oxide (ESRNO), which is a measure of the average of maximum conductance and conductance at 15 seconds after the maximum conductance at a particular electrode, Peak C, which is a maximum conductance reading, and electro skin response latency (ESRL), which is a measure of an amount of time between change of polarity of the galvanic skin response sensor and Peak C, based on the galvanic skin response;

k) calculating a second score based on the ESRNO, ESRL and the Peak C;

l) calculating body mass index (BMI) fat mass based on the bioimpedance;

m) calculating a third score based on the BMI and fat mass;

n) calculating systolic pressure, diastolic pressure and ankle-brachial index (ABI) based on the blood pressure;

o) calculating a fourth score based on the systolic pressure, diastolic pressure and ABI;

p) calculating a homeostatic risk score based on the first, second and third scores that were calculated, wherein the homeostatic risk score corresponds to the homeostatic risk of the patient; and q) displaying the homeostatic risk score on a display.

5. The method of claim 4, wherein the galvanic skin response, bioimpedance, PTG, and blood pressure are received via a communications network communicatively coupled with the computer system.

6. The method of claim 5, wherein the step of calculating a first score further comprises:
calculating a first component score based on PTGTP, stress index, PTGLF, PTGHF;
calculating a second component score based on RI, −da, PEP, LVET, PTGi, PTGVLFi, and PTGr; and
calculating the first score as equal to the first component score plus the second component score.

7. The method of claim 6, wherein the step of calculating a homeostatic risk score further comprises:
calculating the homeostatic risk score as equal to the first score plus the second score plus the third score plus the fourth score.

8. A system for determining homeostatic risk in a patient, in order to screen metabolic diseases and/or their complications and/or their treatment management, the system comprising:
a plurality of sensors coupled with the patient, wherein the plurality of sensors includes: i) a galvanic skin response sensor for measuring galvanic skin response, ii) a bioimpedance sensor for measuring bioimpedance, iii) a pulse oximeter sensor for measuring a photoplethysmogram (PTG), and iv) a blood pressure sensor for measuring blood pressure;
a processor communicatively coupled with the plurality of sensors, the processor configured for:

a) executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG;

b) calculating PTG Total Power (PTGTP) as equal to PTGHF+PTGLF+PTGVLF, c) calculating PTG index (PTGi) of the spectral analysis as equal to amplitude of PTGHF+amplitude of PTGLF+amplitude of PTGVLF;

d) calculating PTG VLF index (PTGVLFi) of the spectral analysis as equal to PTGVLF divided by a value derived from the galvanic skin response;

e) calculating PTG ratio (PTGr) of the spectral analysis as equal to PTGVLF divided by PTGi;

f) calculating a heart rate variability based on the PTG and calculating a stress index based on the heart rate variability;

g) calculating −da as equal to an amplitude of a fourth point of a second derivative of the PTG divided by an amplitude of a first point of the second derivative of the PTG, reflection index (RI), which is a measure of artery stiffness, left ventricular ejection time (LVET) as equal to a time between a global maxima of the PTG, and a dicrotic notch of the PTG, and pre-ejection period (PEP) as equal to a time between a global minima of the PTG and a global maxima of a first derivative of the PTG;

h) calculating a first score based on PTGTP, stress index, PTGLF, PTGHF, RI, −da, PEP, LVET, PTGi, PTGVLFi, and PTGr;

i) calculating electro skin response nitric oxide (ESRNO), which is a measure of an average of maximum conductance and conductance at 15 seconds after the maximum conductance at a particular electrode, Peak C, which is a maximum conductance reading, and electro skin response latency (ESRL), which is a measure of an amount of time between change of polarity of the galvanic skin response sensor and Peak C, based on the galvanic skin response;

j) calculating a second score based on the ESRNO, ESRL and the Peak C;

k) calculating body mass index (BMI) fat mass based on the bioimpedance;

l) calculating a third score based on the BMI and fat mass;

m) calculating systolic pressure, diastolic pressure and ankle-brachial index (ABI) based on the blood pressure;

n) calculating a fourth score based on the systolic pressure, diastolic pressure and ABI;

o) calculating a homeostatic risk score by summing the first, second, third and fourth scores that were calculated, wherein the homeostatic risk score corresponds to the homeostatic risk of the patient; and a display for displaying the homeostatic risk score.

9. The system of claim 8, wherein the step of calculating a first score further comprises:
calculating a first component score based on based on PTGTP, stress index, PTGLF, PTGHF;
calculating a second component score based on RI, −da, PEP, LVET, PTGi, PTGVLFi, and PTGr; and
calculating the first score as equal to the first component score plus the second component score.

10. The system of claim 9, wherein the PTGHF is located in a band between 0.15 and 0.6 Hz, PTGLF is located in a band ranging from 0.04 to 0.15 Hz, and PTGVLF is located in a band lower than 0.04 Hz.

* * * * *